(12) United States Patent
Ebnayamin

(10) Patent No.: US 8,006,709 B1
(45) Date of Patent: Aug. 30, 2011

(54) COMBINED TOOTHPASTE CONTAINER WITH DENTAL FLOSS DISPENSING CAP AND ASSOCIATED METHOD

(76) Inventor: Kamran Ebnayamin, Beverly Hills, CA (US)

(*) Notice: Subject to any disclaimer, the term of this patent is extended or adjusted under 35 U.S.C. 154(b) by 446 days.

(21) Appl. No.: 12/231,847

(22) Filed: Sep. 8, 2008

(51) Int. Cl.
*A61C 15/00* (2006.01)

(52) U.S. Cl. ........................................... 132/325

(58) Field of Classification Search ............... 132/308, 132/309, 311, 323–329
See application file for complete search history.

(56) References Cited

U.S. PATENT DOCUMENTS

| | | | | |
|---|---|---|---|---|
| 1,733,114 A | * | 10/1929 | Brennan | 132/314 |
| 1,858,134 A | * | 5/1932 | Booth et al. | 132/286 |
| 4,673,106 A | | 6/1987 | Fishman | |
| 4,796,783 A | * | 1/1989 | Paulson | 222/80 |
| 4,827,951 A | | 5/1989 | Grussmark | |
| 5,076,302 A | * | 12/1991 | Chari | 132/325 |
| 5,979,706 A | | 11/1999 | Grussmark | |
| 6,547,104 B1 | | 4/2003 | Wilkinson | |
| 7,243,663 B1 | * | 7/2007 | Einstein et al. | 132/314 |

* cited by examiner

*Primary Examiner* — Rachel Steitz

(57) ABSTRACT

The combined toothpaste container and dental floss cap may include a toothpaste container and a removable cap with a hollow chamber and an outlet orifice formed in fluid communication with the hollow chamber. A mechanism for contemporaneously dispensing dental floss and notifying a user when the dental floss is approaching depletion may be situated in the hollow chamber. The mechanism may also include a dental floss spool threaded about a rectilinear worm shaft such that the spool travels along the worm shaft toward a top surface of the cap during dental floss dispensing procedures. An actuating rod with a primary arm and guide arms may be interfitted within the worm shaft and mated with the spool respectively such that the user may selectively access one end of the actuating rod. The actuating rod may rotate during dental floss dispensing procedures and may be oppositely rotated to retract dental floss.

10 Claims, 6 Drawing Sheets

COMBINED TOOTHPASTE CONTAINER WITH DENTAL FLOSS DISPENSING CAP AND ASSOCIATED METHOD

CROSS REFERENCE TO RELATED APPLICATIONS

This application claims the benefit of U.S. Provisional Application No. 60/963,418, filed Aug. 6, 2007, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to the general field products that promote oral hygiene and, more particularly, to a combined toothpaste container and dental floss cap for selectively dispensing predetermined quantities of toothpaste and dental floss respectively.

2. Prior Art

Heretofore, it has been well known that flossing teeth is an important part of the teeth-cleaning process. Dentists highly recommend flossing at least once a day in conjunction with brushing to properly care for teeth and gums. While a large percentage of people brush daily, a much smaller percentage of people floss daily. This failure to floss daily leads to premature tooth decay and eventually the loss of teeth. In response to this problem numerous assemblies have been developed to remind and encourage people to floss during the brushing process. For example, dental floss dispensers have been attached to toothpaste containers in various forms. Unfortunately, most of these applications cause the toothpaste dispenser to become bulky and aesthetically unpleasing, this reducing the likelihood of purchase. Also, the dental floss dispensers are attached in such a way that they can be permanently removed, defeating the purpose of the assembly.

U.S. Pat. No. 4,673,106 to Fishman discloses a dispenser comprising a container having a chamber for retaining a flowable material, and a nozzle defining an outlet orifice. The dispenser has a device for pumping the material through the orifice. The dispenser has a cap having an outwardly directed tab having an opening to receive a toothbrush. The dispenser has a spool rotatably received in a hollow lower base of the container, and an elongated strand of floss wound upon the spool and extending through an opening in the base. Unfortunately, this prior art reference does not provide a means of notifying a user when the spool of dental floss is depleted.

U.S. Pat. No. 4,827,951 to Grussmark discloses a device composed of a dental container having a portion with a dispenser for discharge of a charge of toothpaste and second portion sized to receive a spool of dental floss to be removed through a hole in the container so that a length of the floss can be severed using a cutter on the container. Unfortunately, this prior art reference does not provide a convenient means of replacing dental floss.

U.S. Pat. No. 6,547,104 to Wilkinson discloses a combined toothpaste dispenser and oral hygiene assembly includes a toothpaste dispenser which is preferably a rigid pump. A holder is mounted to the outer component of the pump for detachably housing at least one oral hygiene or personal care tool. Such tool may be a dental floss dispenser and/or toothbrushes. Preferably, a cover is mounted over the top of the dispenser to provide sanitary protection for the dispenser and the personal care tools and to function as a cup as well as enhancing the aesthetic appearance of the assembly. Unfortunately, this prior art reference requires the dental floss dispenser to remain stationary and attached to the toothpaste dispenser.

Accordingly, a need remains for a combined toothpaste container and dental floss cap to over-come the above stated prior art shortcomings. The present invention satisfies such a need by providing an apparatus that is convenient and easy to use, is durable yet lightweight in design, is versatile in its applications, and provides users with a means of selectively dispensing predetermined quantities of toothpaste and dental floss respectively.

BRIEF SUMMARY OF THE INVENTION

In view of the foregoing background, it is therefore an object of the present invention to provide an apparatus for selectively dispensing predetermined quantities of toothpaste and dental floss respectively. These and other objects, features, and advantages of the invention are provided by a combined toothpaste container and dental floss cap.

The combined toothpaste container and dental floss cap preferably includes a toothpaste container. Such a toothpaste container may have a predetermined volume of toothpaste housed therein. A cap may be removably coupled to the toothpaste container. Such a cap preferably has a hollow chamber formed therein. The cap may also have an outlet orifice formed in fluid communication with the hollow chamber.

A mechanism may be included for contemporaneously dispensing dental floss away from the outlet orifice and notifying a user when the dental floss is approaching depletion. The contemporaneous dental floss dispensing and notifying mechanism may be advantageously visible from an exterior of the cap which is vital so that a user may be notified when to refill the dental floss spool.

The contemporaneous dental floss dispensing and notifying mechanism preferably includes a rectilinear worm shaft removably seated inside the hollow chamber. Such a worm shaft may include an axially oriented cavity formed therein and a threaded outer surface. A rectilinear actuating rod with a primary arm may be rotatably interfitted within the axially oriented cavity. Such an actuating rod may have a pair of guide arms extending parallel to the worm shaft. Such guide arms may be situated apart from the worm shaft and may travel parallel to the primary arm respectively such that the guide arms freely slide along the corresponding linear paths defined through said cap respectively.

Further, a spool may be rotatably affixed about the worm shaft and mated with the guide arms respectively. Such a spool may be suitably sized and shaped for effectively releasably maintaining the dental floss at a helically wound stored position inside the hollow chamber. This important feature prevents the dental floss from entangling within the hollow chamber. Additionally, the spool preferably continuously unwinds the dental floss from the stored position when the primary arm and guide arms are synchronously rotated about a centrally registered longitudinal axis passing through the worm shaft.

The cap may be provided with a transparent access door detachably connected thereto. The transparent access door preferably permits the user to maintain a continuous line of sight directly into the hollow chamber as the spool rotates about the worm shaft during dental floss dispensing procedures. This feature is vital so that the user may observe when the dental floss reaches depletion without having to open the access door.

The contemporaneous dental floss dispensing and notifying mechanism preferably further includes a pair of diametrically opposed spring-actuated detents directly connected to a distal end of the worm shaft. Further, the contemporaneous dental floss dispensing and notifying mechanism may include a pair of sockets formed within an interior surface of the cap. The detents are preferably removably interlocked within the sockets when the worm shafts is firmly pressed against the interior surface of the cap such that the worm shaft remains at a static position while the actuating rod and the spool are freely rotated in sync.

The actuating rod and the worm shaft and the spool may be simultaneously removed from the hollow chamber when the detents are disengaged from the sockets and the access door is adapted to an open position during periodic dental floss refill procedures. The refill feature provides for a variety of alternate refill methods, which benefit both the user and the seller.

The access door may further be freely adapted between open and closed positions while the actuating rod and the spool rotate within the hollow chamber respectively. Thus the access door may be removed even when the cap is not in an upright position.

The toothpaste container may have an open proximal end for egressing toothpaste therefrom. The cap is preferably removably coupled to the proximal end of the toothpaste container in such a manner that the toothpaste is prohibited from egressing out from the proximal end while the cap is coupled thereto. Further, the cap may remain at a static and stationary position while the dental floss is dispensed from the outlet orifice which is vital for securing the mechanism during floss dispensing procedures.

The spool may be threadably mated to the worm gear and arranged in such a manner that the spool linearly reciprocates along a linear travel path defined inside the hollow chamber when the primary and guide arms are rotated in first and second arcuate paths respectively. The first and second arcuate paths are preferably defined along clockwise and counter clockwise directions traveling about the longitudinal axis of the actuating rod respectively.

A linear spatial distance between the spool and the access door is respectively decreased and increased as the dental floss egresses and ingresses through the outlet orifice during operating conditions such that a user is visually notified of a depletion rate associated with the dental floss.

The primary arm may be linearly interfitted inside the worm shaft and selectively accessible by the user when the primary arm and the guide arms are freely lifted to an exposed position defined exterior of the access door. Additionally, the primary arm and the guide arms may be linearly displaced with the worm shaft and the spool as the spool rotates about the worm shaft so that the user can adjust the grip of the actuating rod without interrupting the dental floss dispensing operations. In this manner, the actuating rod may be displaced within the cap as not to hinder dispensing operations.

A method for selectively dispensing predetermined quantities of toothpaste and dental floss respectively may include the first step of providing a toothpaste container has a predetermined volume of toothpaste housed therein. The method may also include the second step of providing and removably coupling a cap to the toothpaste container. The cap may have a hollow chamber formed therein and may further have an outlet orifice formed in fluid communication with the hollow chamber.

The method may further include the third step of providing a mechanism for contemporaneously dispensing dental floss away from the outlet orifice and notifying a user when the dental floss is approaching depletion. The contemporaneous dental floss dispensing and notifying mechanism is visible from an exterior of the cap. The method may include the forth and final step of contemporaneously dispensing dental floss away from the outlet orifice and notifying a user when the dental floss is approaching depletion. The dental floss dispensing procedures remain uninterrupted while the cap is removably attached to the toothpaste container.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
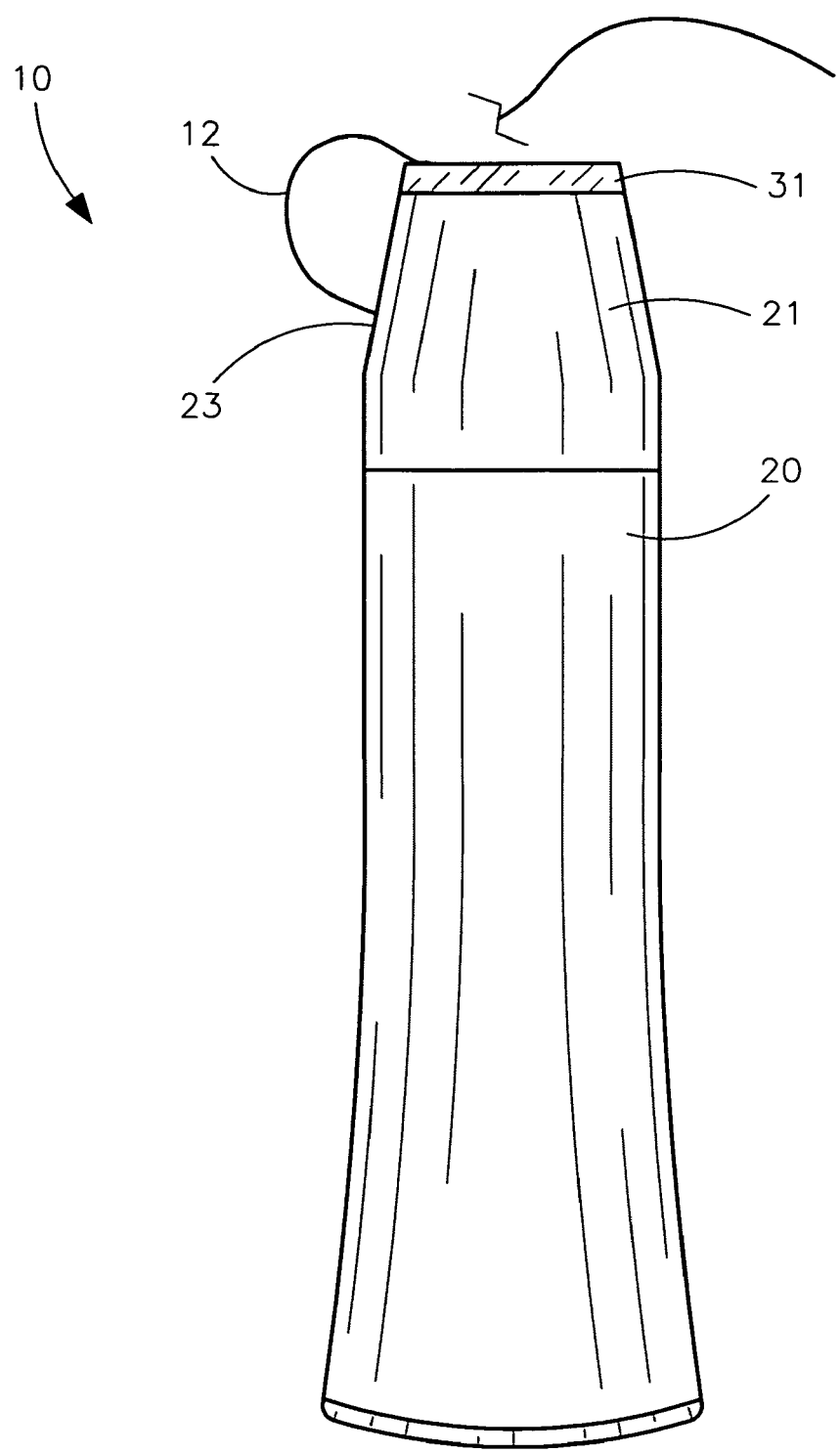
FIG. 1 is a side elevational view showing a combined toothpaste container and dental floss cap, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-4c by the reference numeral 10 and is intended to provide a combined toothpaste container and dental floss cap. It should be understood that the apparatus 10 may be used to for selectively dispensing many different types of toothpaste and dental floss and should not be limited in use to the applications mentioned herein.

Figure 2:
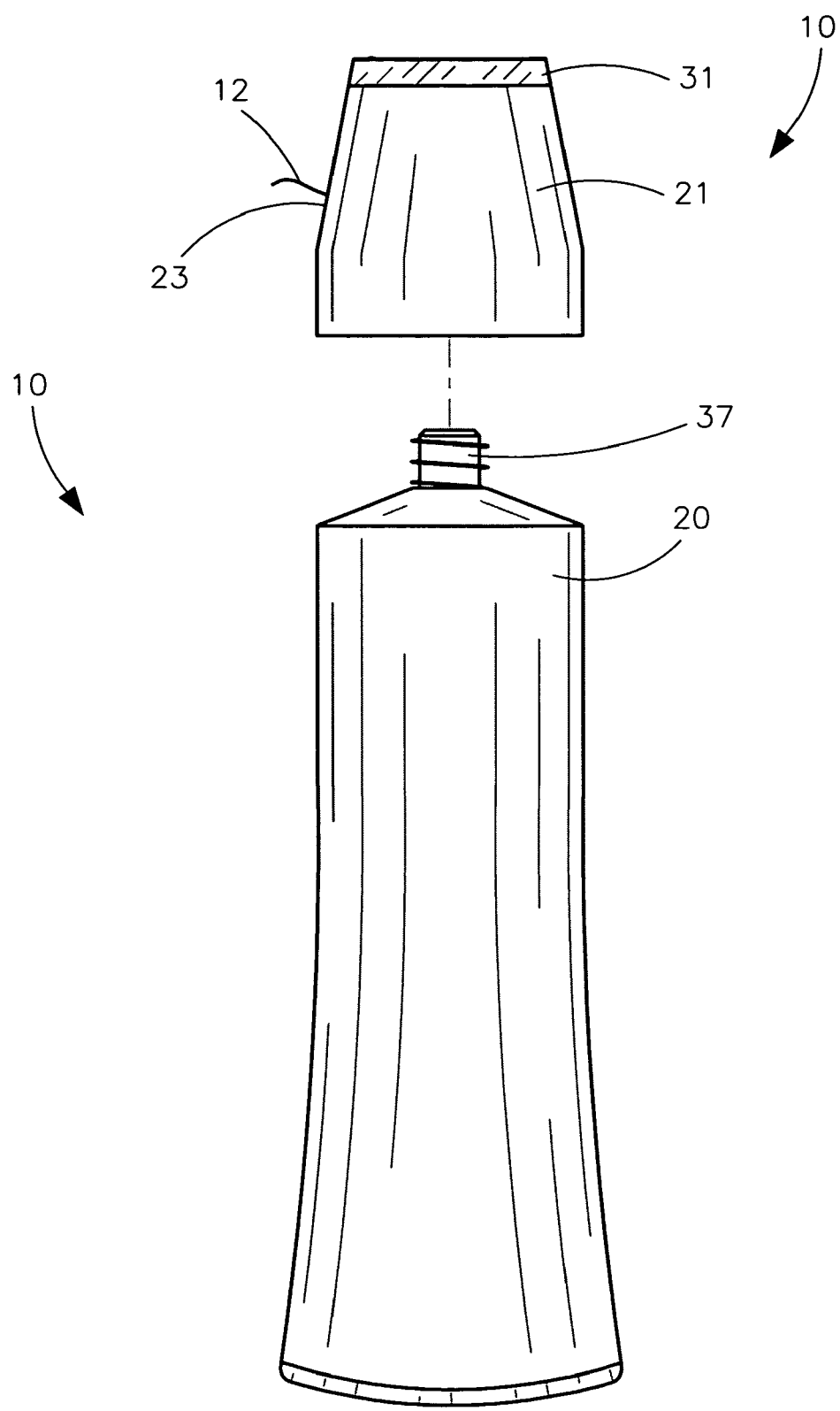
FIG. 2 is a side elevational view showing the apparatus in FIG. 1 with the cap removed from the toothpaste container.
Figure 3:
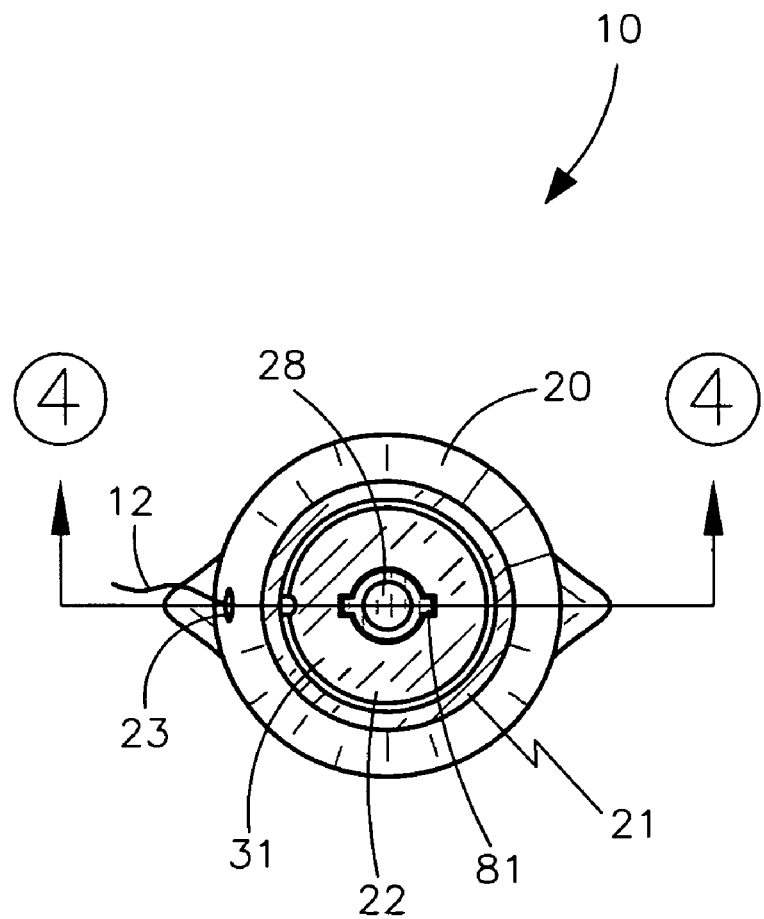
FIG. 3 is a top plan view showing the apparatus in FIG. 1.

Referring initially to FIGS. 1-3, the combined toothpaste container and dental floss cap 10 preferably includes a toothpaste container 20. Such a toothpaste container 20 may have a predetermined volume of toothpaste 11 housed therein. A cap 21 may be removably coupled to the toothpaste container 20. Such a cap 21 preferably has a hollow chamber 22 formed therein. The cap 21 may also have an outlet orifice 23 formed in fluid communication with the hollow chamber 22.

Figure 4A:
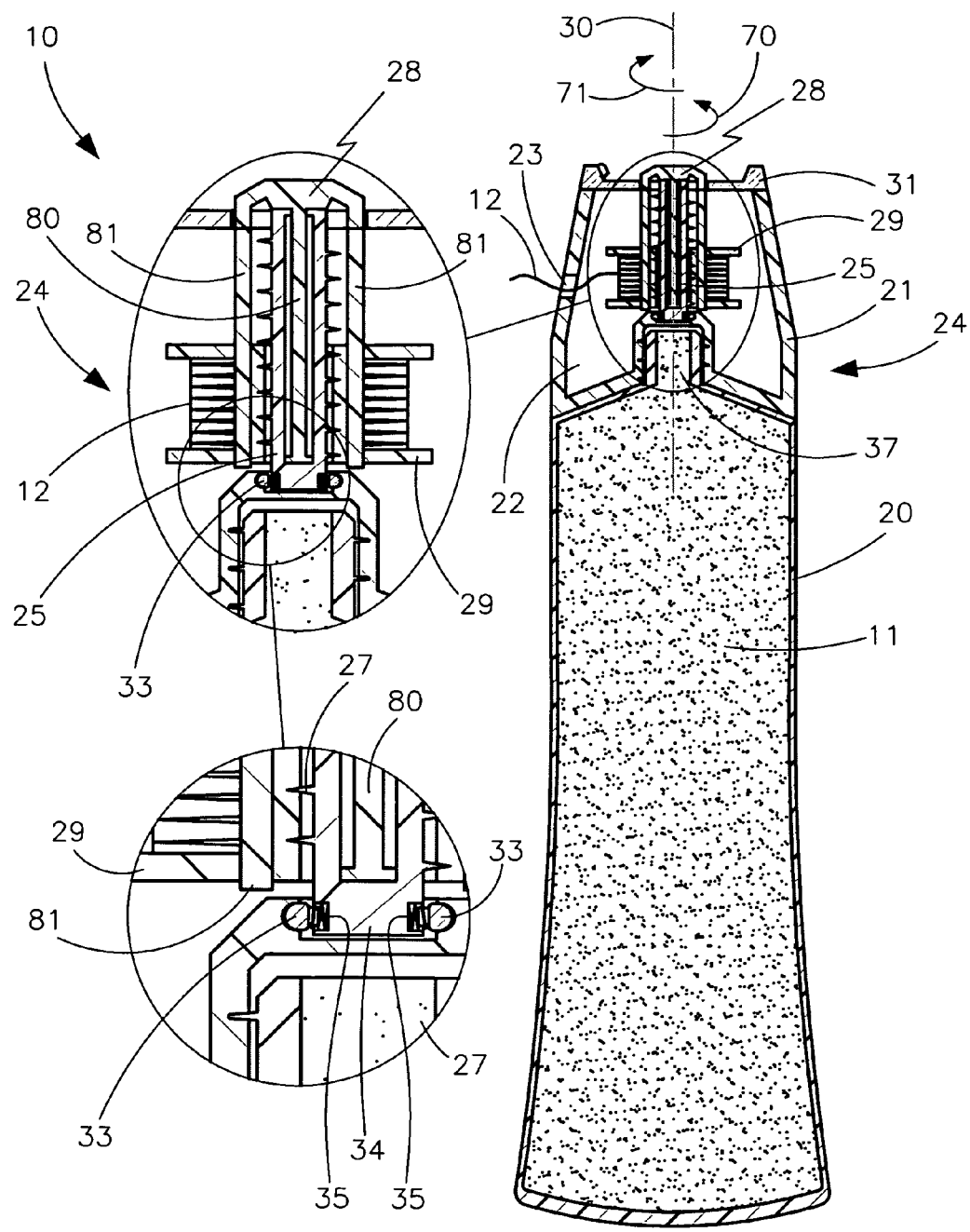
FIG. 4a is a cross section view, taken along line 4-4 in FIG. 3, showing the contemporaneous dental floss dispensing and notifying mechanism with the actuating rod in retracted position.
Figure 4B:
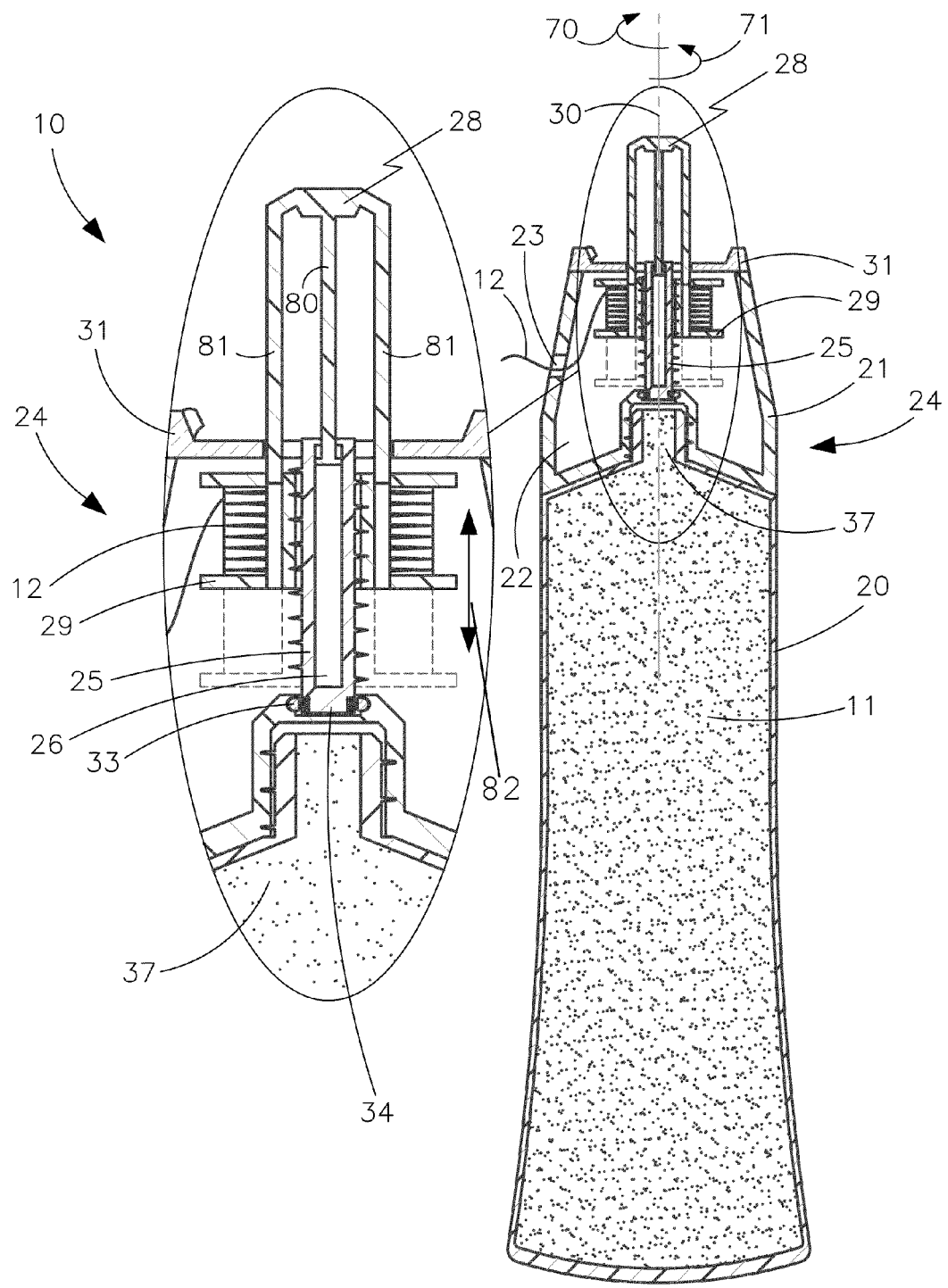
FIG. 4b is a cross section view similar to FIG. 4a showing the actuating rod in an extended position.
Figure 4C:
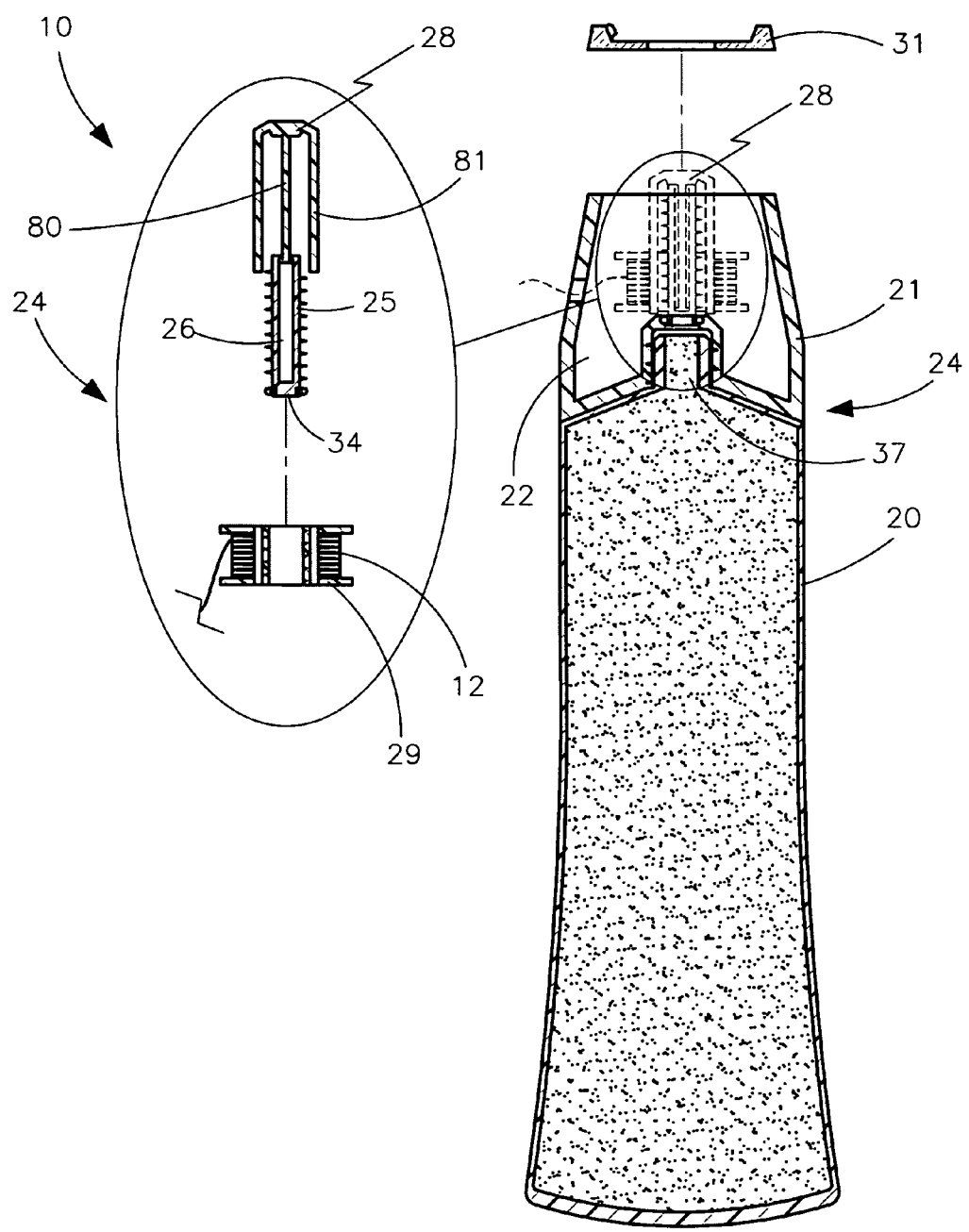
FIG. 4c is a cross section view similar to FIG. 4b showing the worm gear and the actuating rod along with the spool removed from the cap.

Referring to FIGS. 4a-4c, a mechanism 24 may be included for contemporaneously dispensing dental floss 12 away from the outlet orifice 23 and notifying a user when the dental floss 12 is approaching depletion. The contemporaneous dental floss dispensing and notifying mechanism 24 may be advantageously visible from an exterior of the cap 21 which is vital so the user may anticipate when to refill the dental floss.

The combined elements of the toothpaste container 20, the cap 21, and the dental floss dispensing and notifying mechanism 24 provide an unexpected benefit wherein the user receives a reminder to use dental floss during every tooth brushing session. This advantageous feature also saves the user time by overcoming problems associated with independent dental floss dispensers, which are easily misplaced.

Referring to FIGS. 4a-4c, the contemporaneous dental floss dispensing and notifying mechanism 24 preferably includes a rectilinear worm shaft 25 removably seated inside the hollow chamber 22. Such a worm shaft 25 may include an axially oriented cavity 26 (FIG. 4b) formed therein and a threaded outer surface 27. A rectilinear actuating rod 28 with a primary arm 80 may be rotatably interfitted within the axially oriented cavity 26.

The actuating rod 28 may further have a pair of guide arms 81 extending parallel to the worm shaft 25. Such guide arms 81 may be situated apart from the worm shaft 25 and may travel parallel to the primary arm 80 respectively such that the guide arms 81 freely slide along corresponding linear paths 82, defined through the cap 21.

Further, a spool 29 may be rotatably affixed about the worm shaft 25 and mated with the guide arms 81 respectively. Such a spool 29 may be suitably sized and shaped for effectively releasably maintaining the dental floss 12 at a helically wound stored position inside the hollow chamber 22. The spool 29 is important for preventing the dental floss 12 from entangling within the hollow chamber 22. Further, the spool 29 preferably continuously unwinds the dental floss 12 from the stored position when the primary arm 80 and the guide arms 81 are synchronously rotated about a centrally registered longitudinal axis 30 passing through the worm shaft 25.

The guide arms 81 are vital for rotating the spool 29 when the actuating rod 28 rotates. During dental floss dispensing procedures, if the user extracts more dental floss 12 than desired, the user may rotate the actuating rod 28 in an opposite direction from which the actuating rod 28 rotates as dental floss egresses. This retracts the extra dental floss 12 into the cap 21 and winds the dental floss 12 back around the spool 29, saving the user considerable money. Moreover, if the user over-retracts the dental floss 12 such that the floss 12 is no longer visible outside the cap 21, the user may rotate the actuating rod 28 to extend the dental floss 12.

Referring to FIGS. 3-4c, the cap 21 may be provided with a transparent access door 31 detachably connected thereto. The transparent access door 31 preferably permits the user to advantageously maintain a continuous line of sight directly into the hollow chamber 22 as the spool 29 rotates about the worm shaft 25 during dental floss dispensing procedures. This feature is necessary for notifying the user to refill the dental floss 12 when it reaches depletion. In this manner, the user may observe the current level of dental floss 12 wound about the spool 29 without constantly opening the access door 31, thus saving time.

Referring to FIGS. 4a and 4b, the contemporaneous dental floss dispensing and notifying mechanism 24 preferably further includes a pair of diametrically opposed spring-actuated detents 33 directly connected without the use of intervening elements to a distal end 34 of the worm shaft 25. Further, the contemporaneous dental floss dispensing and notifying mechanism 24 may include a pair of sockets 35 formed within an interior surface 36 of the cap 21.

The detents 33 are preferably removably interlocked within the sockets 35 when the worm shaft 25 is firmly pressed against the interior surface of the cap 21 which is necessary so that the worm shaft 25 remains in a static position while the actuating rod 28 and the spool 29 are freely rotated in sync. The worm shaft 25 remaining static within the hollow chamber 22 provides a benefit of allowing the spool 29 to rotate in a smooth manner. This feature enables the center of the spool 29 to remain oriented along the longitudinal axis 30 while the dental floss 12 unwinds therefrom, thus preventing the spool 29 from becoming lodged within the hollow chamber 22 and entangling the dental floss 12.

Referring particularly to FIG. 4c, the actuating rod 28 and the worm shaft 25 and the spool 29 may be simultaneously removed from the hollow chamber 22 when the detents 33 are disengaged from the sockets 35 and the access door 31 is adapted to an open position and removed from the cap 21 during periodic dental floss refill procedures. On skilled in the art knows that detents 33 may be disengaged simply when the user applies sufficient force. By removing the actuating rod 28 and worm shaft 25 and the spool 29 from the hollow chamber 22, the user may easily access and replace the spool 29 without having to maneuver within hollow chamber 22, thus saving time.

Additionally, refills may be in the form of extra spools 29 of dental floss 12 or may be in the form of an extra unit including a combination of the actuating rod 28, the worm shaft 25, and the spool 29. Such refill methods provide a benefit by allowing the user to quickly and conveniently refill the cap 21 with additional dental floss 12. Of course, a line of refill units uniquely fitting particular caps 21 may be created.

Referring to FIGS. 4a-4c, the toothpaste container 20 may have an open proximal end 37 for egressing toothpaste 11 therefrom. The cap 21 is preferably removably coupled to the proximal end 37 of the toothpaste container 20 in such a manner that the toothpaste 11 is prohibited from egressing out from the proximal end 37 while the cap 21 is coupled thereto. Further, the cap 21 may remain at a static and stationary position while the dental floss 12 is dispensed from the outlet orifice 23. In this manner, the user may steadily brace the cap 21 and toothpaste container 20 while dispensing the desired amount of dental floss 12 without inadvertently discharging toothpaste 11 from the toothpaste container 20.

Referring to FIGS. 4a-4b, the spool 29 may be threadably mated to the worm gear 25 and arranged in such a manner that the spool 29 linearly reciprocates along a linear travel path 32 defined inside the hollow chamber 22 when the primary 80 and guide arms 81 are rotated in first 70 and second 71 arcuate paths respectively. The first 70 and second 71 arcuate paths are preferably defined along clockwise and counter clockwise directions traveling about the longitudinal axis 30 of the actuating rod 28 respectively.

Referring to FIGS. 4a and 4b, a linear spatial distance between the spool 29 and of the access door 31 is respectively decreased and increased as the dental floss 12 egresses and ingresses through the outlet orifice 23 during operating conditions such that a user is visually notified of a depletion rate associated with the dental floss 12. For example, the user is notified that the dental floss 12 is completely depleted when the linear spatial distance between the spool 29 and the access door 31 of the cap 21 becomes nominal.

In an alternate embodiment of the present invention, the user may be notified of dental floss 12 depletion when the spool 29 reciprocates along the linear travel path 32 to the point of contacting the access door 31. In other embodiments, the user may be notified when the spool 29 urges the access door 31 into an open position.

Referring particularly to FIG. 4c, the access door 31 may be freely adapted between open and closed positions while the actuating rod 28 and the spool rotate within the hollow chamber 22 respectively. Again, this is vital for refilling dental floss 12 as explained above.

Referring to FIGS. 4a and 4b, the primary arm 80 of the actuating rod 28 may be linearly interfitted inside the worm shaft 25 and selectively accessibly by the user when the primary arm 80 and the guide arms 81 are freely lifted to an exposed position defined exterior of the access door 31. Additionally, the primary arm 80 and the guide arms 81 may be further linearly displaced within the worm shaft 25 and the spool 29 as the spool 29 rotates about the worm shaft 25 so that the user can adjust a grip of the actuating rod 28 without interrupting the dental floss 12 dispensing operations.

Thus, user may displace the primary arm 80 and the guide arms 81 into the worm shaft 25 and the spool 29 respectively when manual rotating of the spool 29 by rotating the actuating rod 28 is not desired. In this manner, the actuating rod 28 remains concealed and will not hinder the dental floss dispensing procedures.

In use, a preferred method for selectively dispensing predetermined quantities of toothpaste and dental floss respectively may include the first step of providing a toothpaste container 20 has a predetermined volume of toothpaste 11 housed therein. The method may also include the second step of providing and removably coupling a cap 21 to the toothpaste container 20. The cap 21 may have a hollow chamber 22 formed therein and further may have an outlet orifice 23 formed in fluid communication with the hollow chamber 22.

The method may further include the third step of providing a mechanism 24 for contemporaneously dispensing dental floss away from the outlet orifice 23 and notifying a user when the dental floss 12 is approaching depletion. The contemporaneous dental floss dispensing and notifying mechanism 24 is visible from an exterior of the cap 21. Finally, the method may include the forth step of contemporaneously dispensing dental floss 12 away from the outlet orifice 23 and notifying a user when the dental floss 12 is approaching depletion. The dental floss 12 dispensing procedures remain uninterrupted while the cap 21 is removably attached to the toothpaste container 20.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A combined toothpaste container and dental floss cap for selectively dispensing predetermined quantities of toothpaste and dental floss respectively, said combined toothpaste container and dental floss cap comprising:

a toothpaste container having a predetermined volume of toothpaste housed therein;

a cap removably coupled to said toothpaste container, said cap having a hollow chamber formed therein and further having an outlet orifice formed in fluid communication with said hollow chamber; and means for contemporaneously dispensing dental floss away from said outlet orifice and notifying a user when the dental floss is approaching depletion;

wherein said contemporaneous dental floss dispensing and notifying means is visible from an exterior of said cap;

wherein said contemporaneous dental floss dispensing and notifying means comprises a rectilinear worm shaft removably seated inside said hollow chamber and having an axially oriented cavity formed therein, said worm shaft further having a threaded outer surface;

a rectilinear actuating rod having a primary arm rotatably interfitted within said axially oriented cavity, said actuating rod further having a pair of guide arms extending parallel to said worm shaft, said guide arms being situated apart from said worm shaft and traveling parallel to said primary arm respectively such that said guide arms freely slide along corresponding linear paths defined through said cap respectively; and a spool rotatably affixed about said worm shaft and mated with said guide arms respectively, said spool being suitably sized and shaped for releasably maintaining the dental floss at a helically wound stored position inside said hollow chamber;

wherein said spool continuously unwinds the dental floss from the stored position when said primary arm and said guide arms are synchronously rotated about a centrally registered longitudinal axis passing through said worm shaft.

2. The combined toothpaste container and dental floss cap of claim 1, wherein said cap is provided with a transparent access door detachable connected thereto, said transparent access door permitting the user to maintain a continuous line of sight directly into said hollow chamber as said spool rotates about said worm shaft during dental floss dispensing procedures.

3. The combined toothpaste container and dental floss cap of claim 2, wherein said contemporaneous dental floss dispensing and notifying means further comprises:

a pair of diametrically opposed spring-actuated detents directly connected to a distal end of said worm shaft; and a pair of sockets formed within an interior surface of said cap, said detents being removably interlocked within said sockets when said worm shaft is firmly pressed against said interior surface of said cap such that said worm shaft remains a static position while said actuating rod and said spool are freely rotated in sync;

wherein said actuating rod and said worm shaft and said spool are simultaneously removed from said hollow chamber when said detents are disengaged from said sockets and said access door is articulated to an open position during periodic dental floss refill procedures.

4. The combined toothpaste container and dental floss cap of claim 1, wherein said toothpaste container has an open proximal end for egressing toothpaste therefrom, said cap being removably coupled to said proximal end of said toothpaste container in such a manner that the toothpaste is prohibited from egressing out from said proximal end while said cap is coupled thereto.

5. The combined toothpaste container and dental floss cap of claim 1, wherein said cap remains at a static and stationary position while the dental floss is dispensed from said outlet orifice.

6. The combined toothpaste container and dental floss cap of claim 2, wherein said spool is threadably mated to said worm gear and arranged in such a manner that said spool linearly reciprocates along a linear travel path defined inside said hollow chamber when said primary and guide arms are rotated in first and second arcuate paths respectively.

7. The combined toothpaste container and dental floss cap of claim 6, wherein said first and second arcuate paths are defined along clockwise and counter clockwise directions traveling about said longitudinal axis of said actuating rod respectively.

8. The combined toothpaste container and dental floss cap of claim 6, wherein a linear spatial distance between said spool and said access door is respectively decreased and increased as the dental floss egresses and ingresses through said outlet orifice during operating conditions such that a user is visually notified of a depletion rate associated with the dental floss.

9. The combined toothpaste container and dental floss cap of claim 2, wherein said access door is freely adapted between open and closed positions while said actuating rod and said spool rotate within said hollow chamber respectively.

10. The combined toothpaste container and dental floss cap of claim 2, wherein said primary arm is linearly interfitted inside said worm shaft and selectively accessible by the user when said primary arm and said guide arms are freely lifted to an exposed position defined exterior of said access door, said primary arm and said guide arms further being linearly displaced within said worm shaft and said spool as said spool rotates about said worm shaft so that a user can adjust a grip of said actuating rod without interrupting the dental floss dispensing operations.

* * * * *